United States Patent
Swain et al.

(10) Patent No.: US 8,734,474 B2
(45) Date of Patent: May 27, 2014

(54) SYSTEM FOR PROVIDING FLUID FLOW TO NERVE TISSUES

(75) Inventors: Larry D Swain, San Antonio, TX (US); Michael E Manwaring, San Antonio, TX (US); Douglas A. Cornet, San Antonio, TX (US); Braden K Leung, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 700 days.

(21) Appl. No.: 12/648,642

(22) Filed: Dec. 29, 2009

(65) Prior Publication Data

US 2010/0168720 A1 Jul. 1, 2010

Related U.S. Application Data

(60) Provisional application No. 61/142,053, filed on Dec. 31, 2008, provisional application No. 61/142,065, filed on Dec. 31, 2008, provisional application No. 61/234,692, filed on Aug. 18, 2009, provisional application No. 61/238,770, filed on Sep. 1, 2009.

(51) Int. Cl.
*A61B 17/08* (2006.01)

(52) U.S. Cl.
USPC .............. 606/152; 601/11; 604/543; 604/313

(58) Field of Classification Search
USPC ........................................... 606/152; 601/11
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

(Continued)

*Primary Examiner* — Melanie Tyson
*Assistant Examiner* — Todd J Scherbel

(57) ABSTRACT

Provided is an apparatus that includes a nerve conduit and a nested manifold for providing a reduced pressure. Also provided is a system that includes a source of reduced pressure, a nerve conduit and nested manifold, and a conduit for providing fluid communication between the manifold and the source of reduced pressure. Additionally provided is a method that includes implanting the above nerve conduit and manifold at a site of damaged nerve tissue and applying a reduced pressure to the manifold thereby stimulating repair or regrowth of nerve tissue.

28 Claims, 6 Drawing Sheets

(56) References Cited

U.S. PATENT DOCUMENTS

| | | |
|---|---|---|
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,778,467 A | 10/1988 | Stensaas et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 6,846,294 B2* | 1/2005 | Rastegar et al. ............ 601/9 |
| 8,257,372 B2* | 9/2012 | Swain et al. ............ 606/152 |
| 8,449,562 B2* | 5/2013 | Swain et al. ............ 606/152 |
| 2002/0077661 A1 | 6/2002 | Saadat |
| 2002/0115208 A1 | 8/2002 | Mitchell et al. |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0146393 A1 | 10/2002 | Bell et al. |
| 2003/0225347 A1 | 12/2003 | Argenta et al. |
| 2004/0186488 A1 | 9/2004 | Droese |
| 2005/0013802 A1 | 1/2005 | Jianwu et al. |
| 2005/0171467 A1* | 8/2005 | Landman ............ 604/35 |
| 2007/0010831 A1 | 1/2007 | Romero-Ortega et al. |
| 2007/0100358 A2 | 5/2007 | Romero-Ortega et al. |
| 2007/0219471 A1* | 9/2007 | Johnson et al. ............ 601/6 |
| 2007/0239066 A1 | 10/2007 | Laham et al. |
| 2008/0275409 A1 | 11/2008 | Kane et al. |
| 2009/0326515 A1* | 12/2009 | Kagan ............ 604/543 |
| 2010/0168625 A1* | 7/2010 | Swain et al. ............ 601/6 |
| 2010/0168870 A1* | 7/2010 | Swain et al. ............ 623/23.72 |
| 2012/0283675 A1* | 11/2012 | Swain et al. ............ 604/319 |
| 2013/0237934 A1* | 9/2013 | Swain et al. ............ 604/290 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 03/101385 A2 | 12/2003 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

(56) References Cited

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinović, V. Đukić, Ž. Maksimović, Đ. . Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

International Search Report and Written Opinion date mailed Aug. 6, 2010 for PCT International Application No. PCT/US2009/069715.

Anderson et al., "Design of Tissue Engineering Scaffolds as Delivery Devices for Mechanical and Mechanically Modulated Signals" Tissue Eng. 13:2525-38 (2007).

Brody et al., "Approaches to Heart Valve Tissue Engineering Scaffold Design" Biomed Mater Res B Appl Biomater. 83:16-43 (2007).

Gemmiti et al., "Fluid Flow Increases Type II Collagen Deposition and Tensile Mechanical Properties in Bioreactor-Grown Tissue-Engineered Cartilage", Tissue Eng. 12:469-79 (2006).

Lago et al., "Neurobiological Assessment of Regenerative Electrodes for Bidirectional Interfacing Injured Peripheral Nerves," IEEE Trans. Biomed. Eng. 54: 1129-37 (2007).

Manwaring et al., Characterization of Rat Meningeal Cultures on Materials of Differing Surface Chemistry, Biomaterials 22:3155-3168 (2001).

Manwaring et al., "Contact Guidance Induced Organization of Extracellular Matrix," Biomaterials 25: 3631-3638 (2004).

Mercier et al., "Poly(lactide-co-glycolide) Microspheres as a Moldable Scaffold for Cartilage Tissue Engineering," Biomaterials 26:1945-1952 (2005).

Mikos et al., "Preparation of Poly(glycolic acid) Bonded Fiber Structures for Cell Attachment and Transplantation," J. Biomed. Mater. Res 27: 183-189 (2004).

(56) References Cited

OTHER PUBLICATIONS

Norman et al., "Methods for Fabrication of Nanoscale Topography for Tissue Engineering Scaffolds," Ann Biomed Eng 34: 89-101(2006).

Pfister et al., "Neural Engineering to Produce in Vitro Nerve Constructs and Neurointerface," Neurosurgery 60: 137-41 (2007).

Sachols et al., "Making Tissue Engineering Scaffolds Work. Review on the Application of Solid Feeform Fabrication Technology to the Production of Tissue Engineering Scaffolds," Eur. Cells and Mat 5:29-40 (2003).

Segvich et al., "Uniform Deposition to Protein Incorporated Mineral Layer on Three-Dimensional Porous Polymer Scaffolds," J. Biomed Mater Res B: Appl. Biomater 84B: 340-349 (2008).

Shimko et al., "Effect of Porosity on the Fluid Flow Characteristics and Mechanical Properties of Tantalum Scaffolds," J. Biomed Mater Res B: Appl Biomater 73:315-24 (2005).

Takahashi et al., "Induction of Pluripotent Stem Cells from Mouse Embryonic and Adult Fibroblast Cultures by Defined Factores," Cell 126:663-76 (2006).

Tan et al., "Osteocytes Subjected to Fluid Flow Inhibit Osteoclast Formation and Bone Resorption," Bone 41:745-751 (2007).

Tan et al., "Inhibition of Osteocyte Apoptosis by Fluid Flow is Mediated by Nitric Oxide," Biochem Biophys Res Comm 369: 1150-1154 (2008).

Walsh et al., "Directional Neurite Outgrowth is Enhanced by Engineered Meningeal Cell-Coated Substrates," Tissue Eng. 11:1085-1094 (2005).

International Preliminary Report on Patentability issued on Jul. 5, 2011 for PCT/US2009/069715.

European Search Report and Written Opinion date mailed Aug. 3, 2012 for European Application No. 09837120.6.

International Search Report and Written Opinion date mailed Aug. 19, 2010 for PCT Application No. PCT/US2009/069713.

International Search Report and Written Opinion date mailed Aug. 19, 2010 for PCT Application No. PCT/US2009/069710.

Ma PX and Elisseeff J. ed. Scaffolding in Tissue Engineering, CRC, ISBN 1574445219 (2005); pp. 13-25, 189-197 and 585-608.

Saltzman WM, Tissue Engineering: Engineering Principles for the Design of Replacement Organs and Tissues, Oxford ISBN 019514130X (2004); pp. 318-347; 348-385 and 453-484.

Wen X et al., pp. 1-23 in Handbook of Nanostructured Biomaterials and Their Applications in Nanobiotechnology, H.S. Nalwa, ed. ISBN 1-58883-033-0 (2005); pp. 393-414.

\* cited by examiner

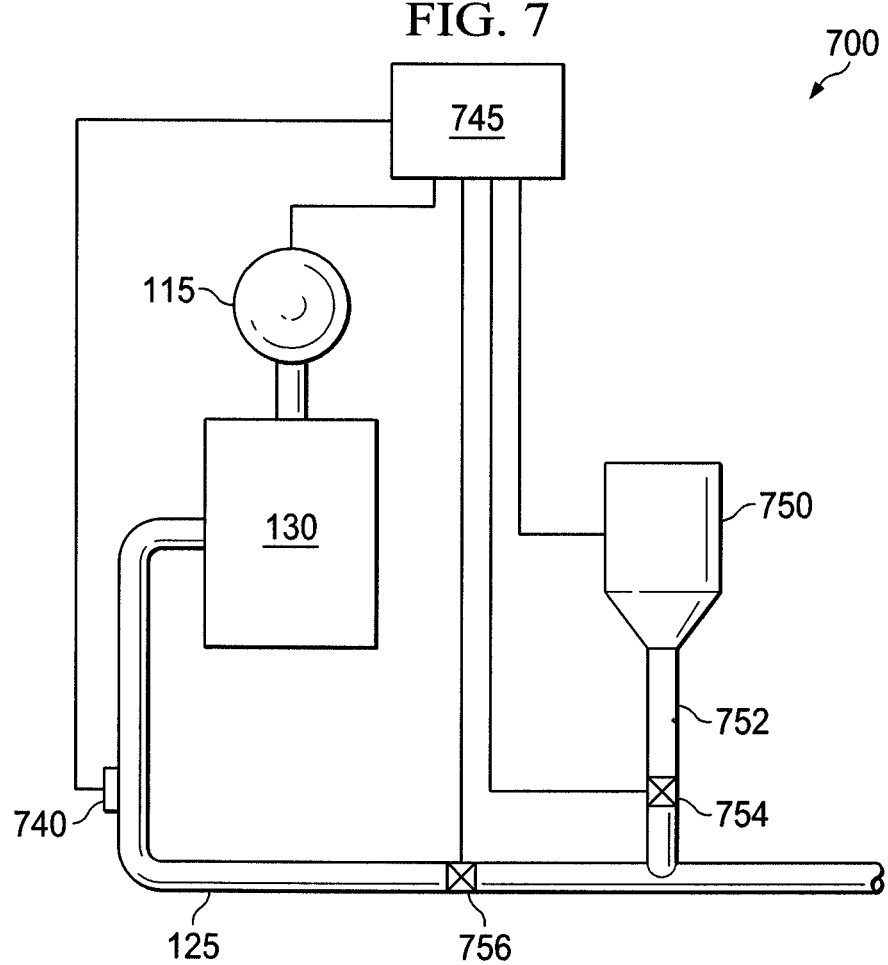

SYSTEM FOR PROVIDING FLUID FLOW TO NERVE TISSUES

This application claims priority to U.S. Provisional Application Nos. 61/142,053 and 61/142,065, each filed on Dec. 31, 2008. This application also claims priority to U.S. Provisional Application No. 61/234,692, filed on Aug. 18, 2009 and U.S. Provisional Application No. 61/238,770, filed on Sep. 1, 2009. Each of the foregoing applications is incorporated herein by reference in their entirety.

BACKGROUND

1. Field of the Invention

The present application relates generally to tissue engineering and in particular to apparatuses and systems suitable for use in treatment of damaged nerve tissue.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formation of granulation tissue. Typically, reduced pressure has been applied to tissue through a porous pad or other manifolding device. The porous pad contains pores that are capable of distributing reduced pressure to the tissue and channeling fluids that are drawn from the tissue. The porous pad often is incorporated into a dressing having other components that facilitate treatment. A scaffold can also be placed into a defect to support tissue growth into the defect. The scaffold is usually bioabsorbable, leaving new tissue in its place.

Scaffolds for reduced pressure treatment are described in, e.g., WO08/091,521, WO07/092,397, WO07/196,590, WO07/106,594. The adequacy of current scaffolds for reduced pressure treatment can be evaluated in light of current knowledge of wound healing. Injury to body tissues results in a wound healing response with sequential stages of healing that include hemostasis (seconds to hours), inflammation (hours to days), repair (days to weeks), and remodeling (weeks to months). A high level of homology exists across most tissue types with regards to the early phases of the wound healing process. However, the stages of healing for various tissues begin to diverge as time passes, with the involvement of different types of growth factors, cytokines, and cells. The later stages of the wound healing response are dependent upon the previous stages, with increasing complexity in the temporal patterning of and interrelationships between each component of the response.

Strategies to facilitate normal repair, regeneration, and restoration of function for damaged tissues have focused on methods to support and augment particular steps within this healing response, especially the latter aspects of it. To this end, growth factors, cytokines, extracellular matrix (ECM) analogs, exogenous cells and various scaffolding technologies have been applied alone or in combination with one another. Although some level of success has been achieved using this approach, several key challenges remain. One main challenge is that the timing and coordinated influence of each cytokine and growth factor within the wound healing response complicate the ability to add individual exogenous factors at the proper time and in the correct coordination pattern. The introduction of exogenous cells also faces additional complications due to their potential immunogenicity as well as difficulties in maintaining cell viability.

Synthetic and biologic scaffolds have been utilized to provide three-dimensional frameworks for augmenting endogenous cell attachment, migration, and colonization. To date nearly all scaffolds have been designed with the idea that they can be made to work with the biology. Traditional scaffolding technologies, however, rely on the passive influx of endogenous proteins, cytokines, growth factors, and cells into the interstitium of the porous scaffold. As such, the colonization of endogenous cells into the scaffold is limited by the distance away from vascular elements, which provide nutrient support within a diffusion limit of the scaffold, regardless of tissue type. In addition, the scaffolds can also elicit an immunogenic or foreign body response that leads to an elongated repair process and formation of a fibrous capsule around the implant. Taken together, these complications can all lead to less than functional tissue regeneration at the injury site.

It would therefore be advantageous to provide additional systems for the repair and remodeling of specialized tissues. The present invention provides such systems.

SUMMARY

The apparatuses, systems and methods of the illustrative embodiments described herein provide active guidance of nerve tissue repair and regeneration through an implanted manifold and nerve conduit. In one embodiment, an apparatus for providing reduced pressure therapy and facilitating growth of nerve tissue in a patient is provided that includes a nerve conduit and nested manifold adaptable for implantation at a damaged nerve site, wherein the manifold provides and distributes reduced pressure at the site of damaged nerve tissue. A manifold according to the invention may also be coupled to a scaffold material which further distributes reduced pressure and provides a structural matrix for growth of the tissue.

In another embodiment, a system for providing reduced pressure therapy and facilitating growth of nerve tissue in a patient is provided that comprises a source of reduced pressure for supplying reduced pressure and a manifold nested in a nerve conduit adaptable for implantation at the tissue site, where the manifold is in fluid communication with the source of reduced pressure. Such a system may also comprise a scaffold material coupled to the manifold which further distributes reduced pressure and provides a structural matrix for the growth of nerve tissue. In a further embodiment, such a system may further comprise a canister for fluid capture and/or a valve for control of reduced pressure in fluid communication with, and positioned between, the manifold and the reduced pressure source. In still a further embodiment, a system according to the invention further comprises a fluid source in fluid communication with the manifold and the damaged nerve tissue.

In a further embodiment, a method of providing reduced pressure therapy and facilitating growth of nerve tissue at a site of nerve tissue damage in a patient is provided that includes implanting a nerve conduit and nested manifold at the tissue site, where the manifold provides a reduced pressure to the damaged nerve tissue. The manifold may also be coupled to a scaffold material, wherein the scaffold material provides a structural matrix for the growth of the nerve tissue. In certain embodiments, the method further comprises providing a manifold in fluid communication with a fluid source, wherein the fluid source may be used to deliver a fluid to the manifold and the damaged nerve tissue. In yet a further embodiment, the fluid source may comprise a fluid comprising one or more bioactive compounds including, but not limited to, an antibiotic, an antiviral, a cytokine, a chemokine, an antibody, and a growth factor.

Other objects, features, and advantages of the illustrative embodiments will become apparent with reference to the drawings and detailed description that follow.

BRIEF DESCRIPTION OF THE DRAWINGS

FIG. 7 is a schematic view of a fluid control system for the system shown in FIGS. 1 and 2.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
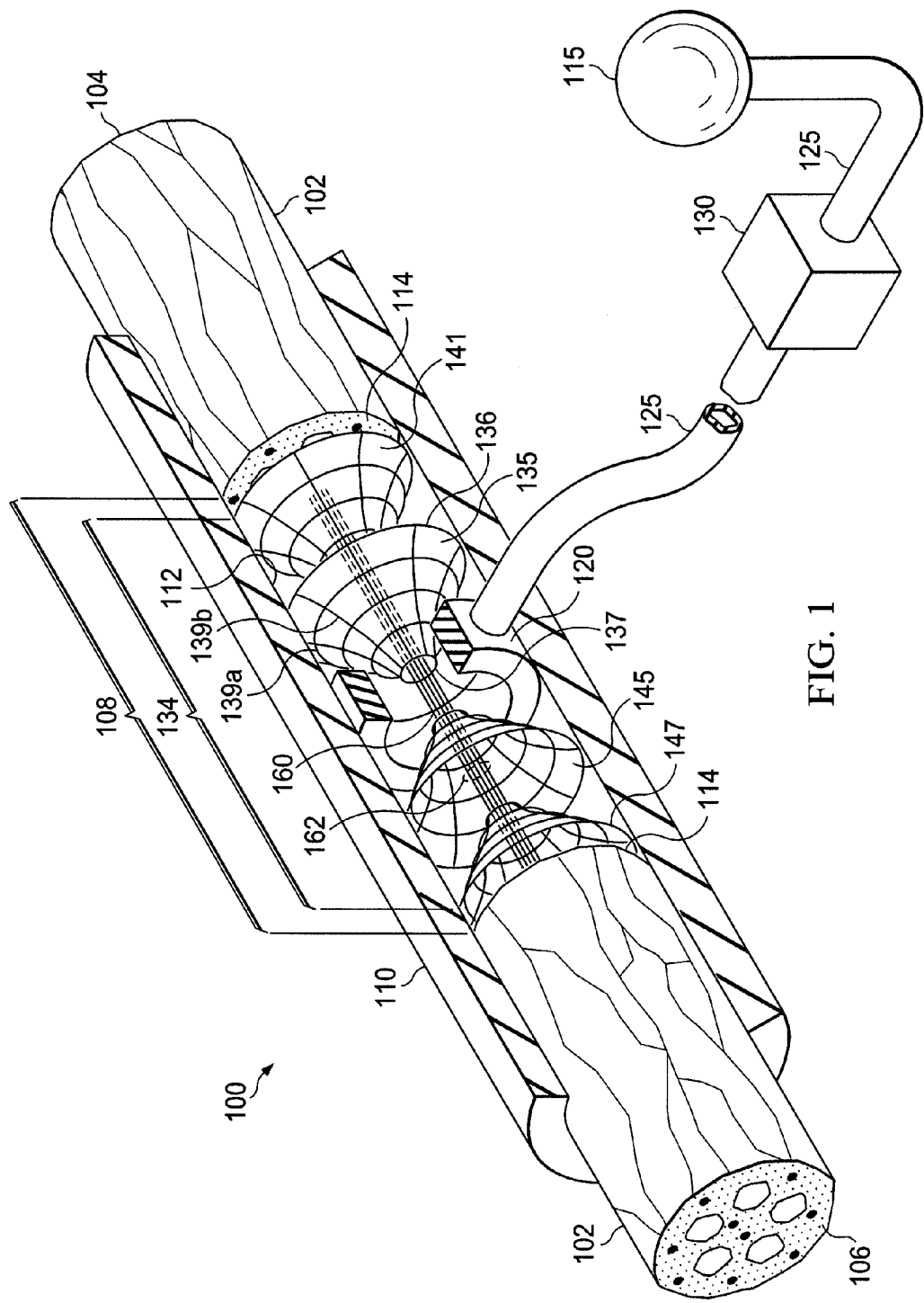
FIG. 1 is a schematic, perspective view of a reduced-pressure system for repairing a severed nerve including a nerve conduit and a first embodiment of a manifold and a scaffold having fiber guides with a section of the nerve conduit removed to show the manifold and scaffold.

Referring to FIG. 1, a reduced pressure therapy system 100 for applying reduced pressure at a tissue site in the body of a patient to repair a defect such as, for example, a damaged nerve is disclosed. The damaged nerve may have been pinched, partially disconnected or severed, or partially degenerated as a result of disease. For example, the damaged nerve in FIG. 1 is a severed nerve 102 having a proximal segment 104 and a distal segment 106 relative to the central nervous system (CNS) of the patient. The severed nerve 102 has been damaged at a nerve damage site 108 that has been severed or degenerated. The severed nerve 102 may be branched or unbranched at the nerve damage site 108. The term "nerve damage site" as used herein refers to a wound or defect located on or within any nerve tissue, including, but not limited to, a disconnected or partially disconnected nerve, a degenerated or partially degenerated nerve, and a compressed or pinched nerve. For example, reduced pressure tissue treatment may be used to enhance repair or regrowth of existing nerve tissue or to facilitate growth or grafted or transplanted nerve tissue and/or cells.

The reduced pressure therapy system 100 comprises a nerve conduit 110 that surrounds the severed nerve 102 at the nerve damage site 108 with a section of the nerve conduit 110 removed to show the nerve damage site 108. The nerve conduit 110 is substantially tubular in shape and closes the nerve damage site 108 and a portion of the proximal segment 104 and the distal segment 106 that has not been damaged. The nerve conduit 110 has an inner surface 112 that forms a nerve gap 114 with the surface of the nerve damage site 108, i.e., a luminal space between the inner surface 112 of the nerve conduit 110 and the surface of the nerve damage site 108. The reduced pressure therapy system 100 also comprises a reduced pressure source 115 for providing a reduced pressure and a manifold 120 fluidly coupled to the reduced pressure source 115 via a first conduit 125. The manifold 120 is generally tubular or cylindrical in shape (see, e.g., the manifold disclosed in copending U.S. patent application Ser. No. 12/648,463, incorporated herein by reference) and positioned within the nerve gap 114. The manifold 120 may have a variety of shapes depending on the type of nerve damage, and in this particular embodiment has a tubular shape to occupy a portion of the nerve gap 114. The manifold 120 may also contain scaffold structure 134 that provides structure for tissue growth and repair. The reduced pressure therapy system 100 further comprises a canister 130 fluidly coupled between the reduced pressure source 115 and the manifold 120 via the first conduit 125 to collect bodily fluids such as blood or exudate that are drawn from the scaffold structure 134 and the nerve gap 114. In one embodiment, the reduced pressure source 115 and the canister 130 are integrated into a single housing structure.

Figure 2:
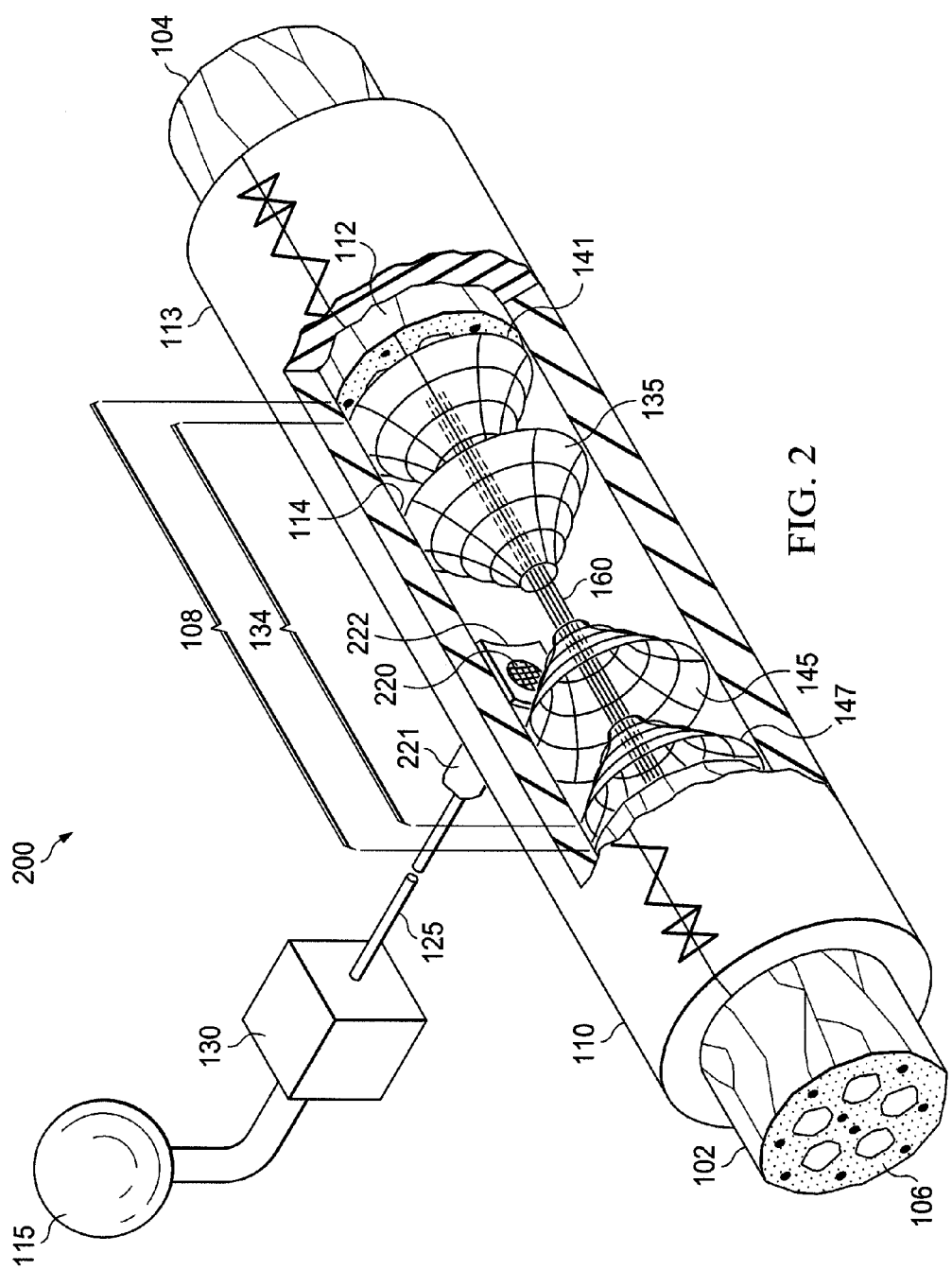
FIG. 2 is a schematic, perspective view of a reduced-pressure system of for repairing a severed nerve including a nerve conduit and a second embodiment of a manifold and scaffold having fiber guides with a section of the nerve conduit removed to show the manifold.

A further embodiment of a reduced-pressure system 200 is shown in FIG. 2 and is substantially similar to the reduced-pressure system 100. The reduced pressure therapy system 200 comprises a nerve conduit 110 that surrounds the severed nerve 102 at the nerve damage site 108 with a section of the nerve conduit 110 removed to show the nerve damage site 108. The nerve conduit 110 is substantially tubular in shape and closes the nerve damage site 108 and a portion of the proximal segment 104 and the distal segment 106 that has not been damaged. The nerve conduit 110 has an exterior surface 113 and an inner surface 112 that forms a nerve gap 114 with the surface of the nerve damage site 108, i.e., a luminal space between the inner surface 112 of the nerve conduit 110 and the surface of the nerve damage site 108. The reduced-pressure system 200 also comprises a reduced pressure source 115 for providing a reduced pressure and a manifold 220 fluidly coupled to the pressure source 115 via a first conduit 125. The manifold 220 (see, e.g., the manifold disclosed in copending U.S. patent application Ser. No. 12/648,458, incorporated herein by reference) is contained within a manifold chamber 221 having a flange 222 extending from one end of the manifold chamber 221 for securing the manifold chamber 221 to the nerve conduit 110. The other end of the manifold chamber 221 is connected to the first conduit 125 so that the manifold 220 is held in fluid communication with the first conduit 125. The manifold chamber 221 may be constructed of any biocompatible material that is substantially impermeable to preserve the manifold's 220 fluid communication between the nerve gap 114 and the first conduit 125. The manifold chamber 221 is secured to the nerve conduit 110 by the flange 222 such that the manifold 220 is in fluid communication with the nerve gap 114 surrounding the surface of the nerve damage site 108, but positioned outside of the nerve gap 114. In certain aspects the flange 222 is secured to the nerve conduit 110 with an adhesive. Moreover, in some applications, the flange 222 is detachably secured to the nerve conduit 110 such that the flange 222 and manifold chamber 221 can be removed from the nerve conduit 110 after reduced pressure therapy is complete. In one embodiment, the manifold 220 extends through the wall of the nerve conduit 110 in direct fluid contact with the nerve gap 114. In another embodiment, where the nerve conduit 110 is porous, the flange 222 is secured to the exterior surface 113 of the nerve conduit 110 so that the manifold 220 is positioned adjacent to the exterior surface 113 to be in fluid communication with the nerve gap 114 via the porous wall of the nerve conduit 110.

As used herein, the term "coupled" includes direct coupling or indirect coupling via a separate object. The term "coupled" also encompasses two or more components that are continuous with one another by virtue of each of the components formed from the same piece of material. Also, the term "coupled" may include chemical, mechanical, thermal, or electrical coupling. Fluid coupling means that fluid is in communication with designated parts or locations.

In the context of this specification, the term "reduced pressure" generally refers to a pressure that is less than the ambient pressure at a tissue site that is subjected to treatment. In most cases, this reduced pressure will be less than the atmospheric pressure of the location at which the patient is located. Although the terms "vacuum" and "negative pressure" may be used to describe the pressure applied to the tissue site, the actual pressure applied to the tissue site may be significantly greater than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure. The term "−Δp" means change in reduced pressure. As used herein, a greater (i.e., more negative) −Δp means increased negative pressure (i.e., a greater change in pressure from ambient pressure). Reduced pressure treatment typically applies reduced pressure at −5 mm Hg to −500 mm Hg, more usually −5 to −300 mm Hg, including but not limited to −50, −125 or −175 mm Hg. Reduced pressure may be constant at a particular pressure level or may be varied over time. For example, reduced pressure may be applied and stopped periodically or ramped-up or -down overtime.

Figure 3:
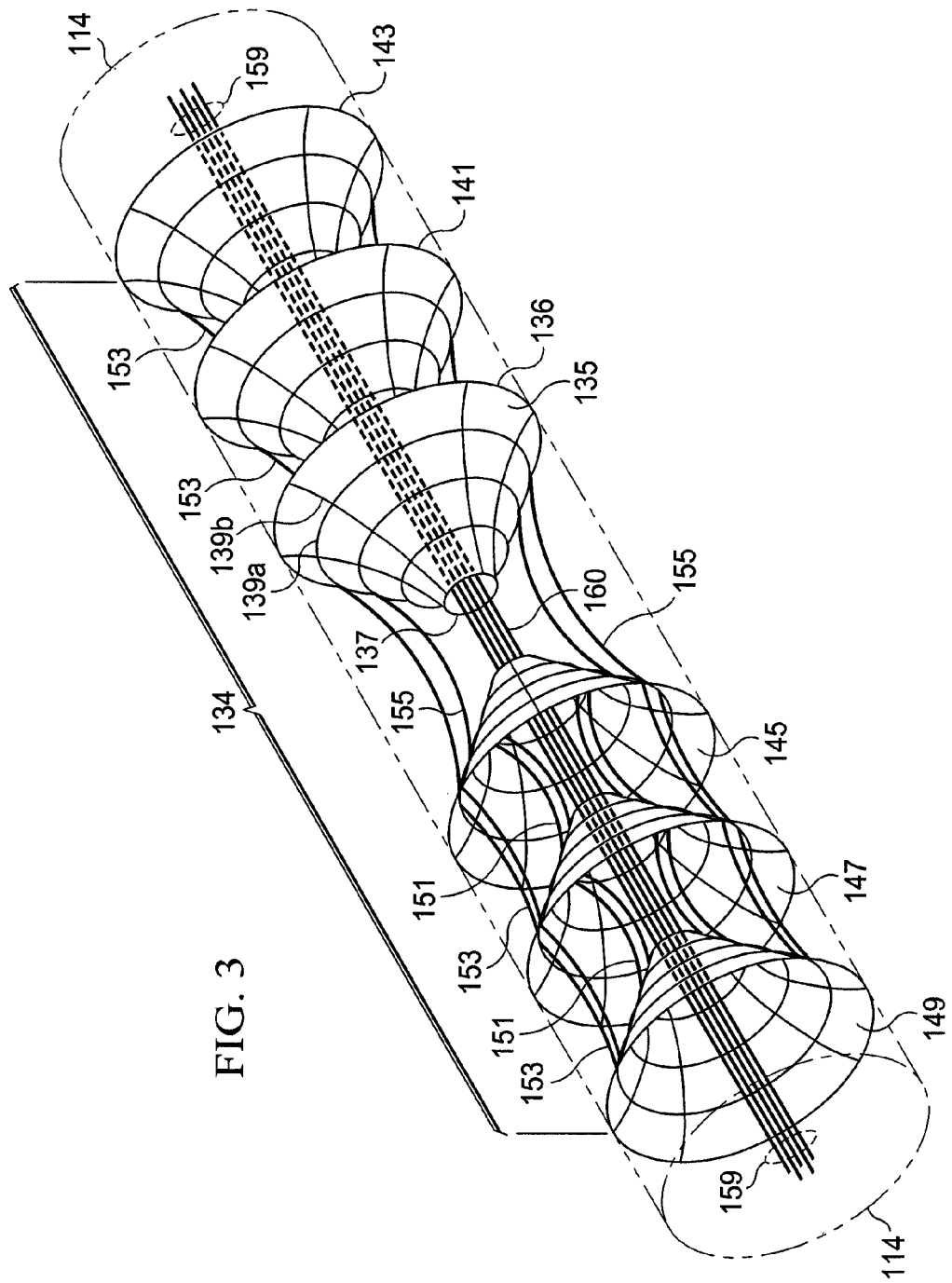
FIG. 3 is a schematic, perspective view of the scaffold and fiber guides of the reduced-pressure systems shown in FIGS. 1 and 2.

Referring to FIGS. 1-3 and the manifolds 120 and 220 collectively as manifold 20 for ease of explanation, the systems 100 and 200 further comprise a scaffold structure 134 including one or more scaffold guides positioned within the nerve gap 114 in fluid communication with the manifold 20 on one or both sides of the manifold 20 such as, for example, scaffold guide 135. The scaffold guide 135 has a generally frusto-tubular shape with a base opening 136 at the base end of the frustum and a vertex opening 137 at the other end of the frustum. The scaffold guide 135 is positioned in the nerve gap 114 and oriented therein so that the vertex opening 137 is positioned closer to the manifold 20 than the base opening 136 which faces the proximal segment 104 when the vertex opening 137 is on the proximal side of the manifold 20 or faces the distal segment 106 when the vertex opening 137 is on the distal side of the manifold 20. More specifically, the scaffold structure 134 of the systems 100, 200 comprise six scaffold guides (only four shown in FIGS. 1 and 2) including scaffold guides 135, 141, 143, 145, 147, and 149 (collectively the "scaffold guides") wherein the scaffold guides 135, 141, and 143 are positioned on the proximal side of the manifold 20 so that their vertex openings are closer to the manifold 20 than their base openings which face the proximal segment 104. A system according to the invention may, however, comprise 1, 2, 3, 4, 5, 6, 7, 8 or more scaffold guides. Correspondingly, the scaffold guides 145, 147, and 149 are positioned on the distal side of the manifold 20 so that their vertex openings are closer to the manifold 20 than their base openings which face the distal segment 106. The scaffold guides may be formed of a scaffold fabric material or a web-like material 139 as illustrated by the concentric rings 139a and ribs 139b. In either embodiment, the scaffold guides function as nodes within the nerve gap 114 for protein absorption and the initialization point for fibril formation. The structure of the scaffold guides also wicks and directs slow-moving fluid within the nerve gap 114 from the base opening 136 toward the vertex opening 137 and the source of the reduced pressure, i.e., the manifold 20. The scaffold guides may be composed of any biocompatible material, but is preferably a bioabsorbable material.

The scaffold structure 134 may further comprise one or more fiber guides 160 extending through the vertex openings of each of the scaffold guides from the proximal segment 104 to the distal segment 106 of the severed nerve 102. The fiber guides 160 may form a fiber bundle 159 also extending between the proximal segment 104 and the distal segment 106 including, but not limited to, as many as one hundred fiber guides 160. The fiber guides 160 may also be fluidly and/or mechanically coupled to the proximal segment 104 and/or the distal segment 106 of the severed nerve 102. Additionally, the fiber guide 160 may be fluidly and/or mechanically coupled to the manifold 20. When fibril formation commences as described above, the scaffold guides wick and direct fluid toward the vertex openings of the scaffold guides and the fiber guides 160 which facilitate fibril formation between the scaffold guides and ultimately extending between the base openings of the scaffold guides. Referring more specifically to FIG. 3, fibril formation commences with direct fluid flow toward the vertex openings of the scaffold guides and along the fiber guides 160 as indicated by the fibers 151 that grow along the path created by the fiber guides 160. The fibers 151 may constitute either provisional matrix fibers such as but not limited to fibrin, collagens, proteoglycans, and laminin, or cellular based structures such as nerve fibers or supportive cell types. The provisional matrix and cellular based fibers may be derived either from endogenous host sources, or from the introduction of exogenous fluids. As fibril formation increases the density of the fibers 151, fibril formation expands outwardly between the base openings of the scaffold guides as indicated by fibers 153. Ultimately, fibers 155 begin forming between the scaffold guides having vertex openings facing each other, e.g., scaffold guides 135 and 145. The fiber guides 160 act to guide cell migration and growth through the entire scaffold structure 134 and may be composed of any biocompatible material such as a bioabsorbable material. In certain cases, the fiber guides are composed of a biological material such as collagen or fibrin.

Figure 4:
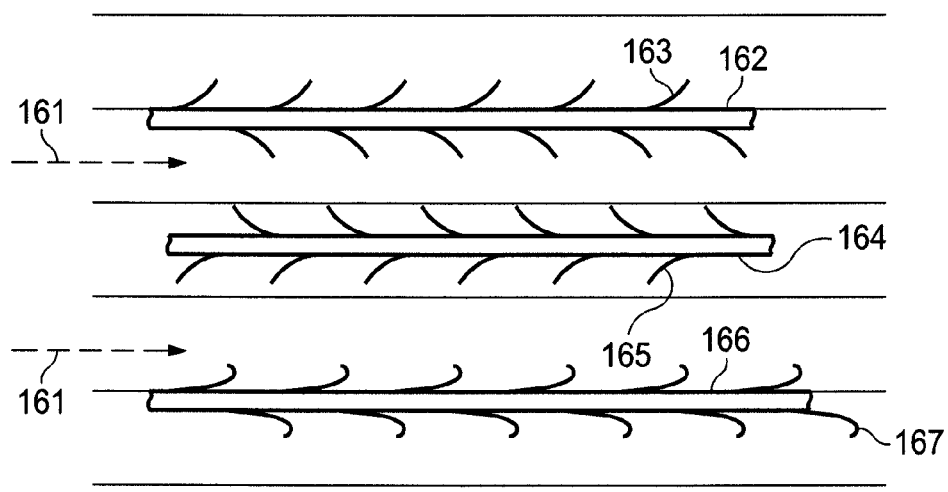
FIG. 4 is a schematic, side view of three embodiments of the fiber guides shown in FIG. 3.
Figure 5:
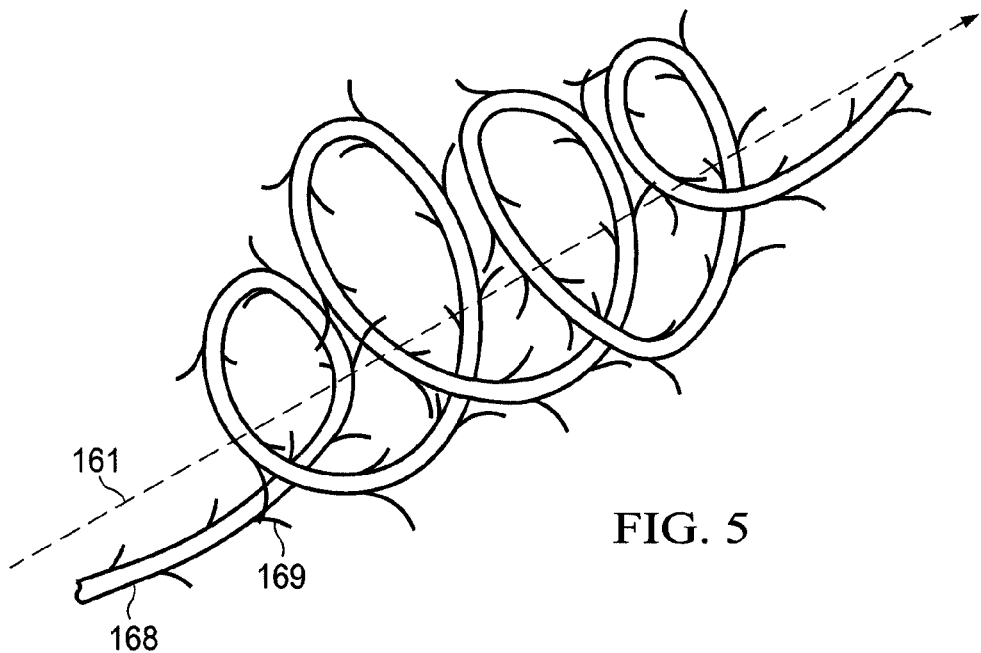
FIG. 5 is a schematic, perspective view of a fourth embodiment of the fiber guides shown in FIG. 3.

Referring now to FIGS. 3 and 4, three embodiments of a fiber guide 160 with fluid flowing in a direction indicated by the dashed arrows 161 are shown including fiber guides 162, 164, and 166. Each of the fiber guides 162, 164, and 166 comprise a strand of fiber material including protrusions for binding of proteins and cells from the slow-moving fluid within the nerve gap 114 to facilitate fibril formation. More specifically, fiber guides 162 and 164 include small barbs 163 and 165 extending from the strands of the fibril guides 162 and 164 in a direction with fluid flow and against fluid flow, respectively, depending upon the fluidics within the nerve gap 114. Alternatively, the fiber guide 166 includes protrusions in the shape of hooks 167 to facilitate protein binding and initiation sites of fibril formation through the nerve gap 114 without being aligned against fluid flow as are the small barbs 165 of the fiber guide 164. The the small barbs 163 and 165 and the hooks 167 may also be oriented in a direction extending either toward the proximal segment 104 or the distal segment 106 of the severed nerve 102 as may be required by the fluidics within the nerve gap 114. In general, the fiber guides 162, 164, and 166 including their the small barbs 163 and 165 and hooks 167, respectively, are composed of the same materials described for use in other scaffold materials such as, for example, collagen or fibrin. Referring to FIG. 5, a fiber guide 160 may comprise a strand of fiber material that has a form other than the linear form described above and shown in FIG. 4. For example, the strand of a fiber guide 168 is shaped in the form of a spiral having a longitudinal axis substantially parallel to the flow of fluid through the nerve gap 114 as indicated by dashed arrow 161. The fiber guide 168 may also have protrusions extending from the strand such as, for example, barbs 169 which are similar to the small barbs 163 of the fiber guide 162.

Figure 6:
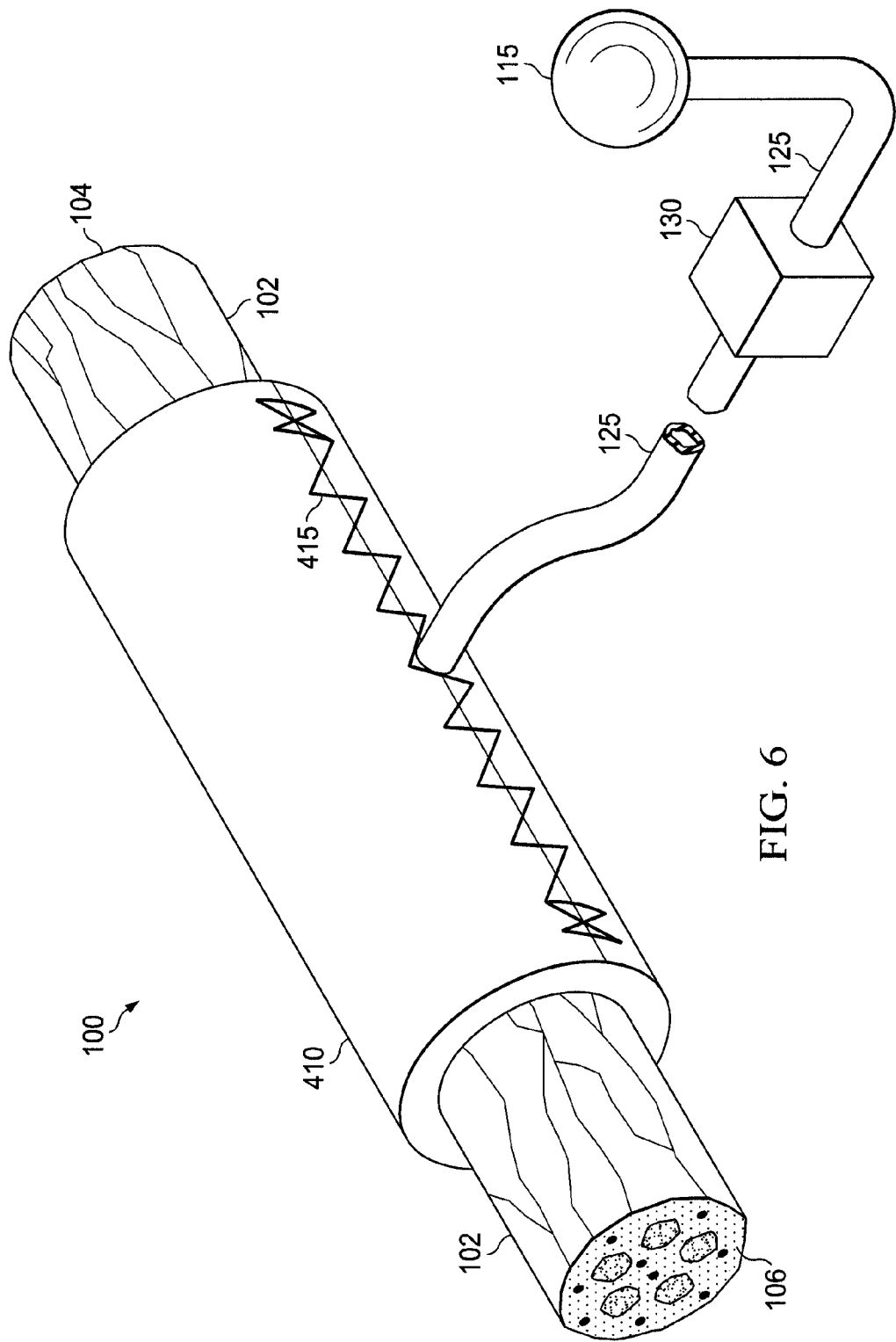
FIG. 6 is a schematic, perspective view of the system in FIGS. 1 and 2 showing the nerve conduit enclosing the damaged nerve.

The nerve conduit 110 is shown in FIGS. 1 and 2 with a section removed to show the manifolds 120, 220 and is shown as completely surrounding the nerve damage sites 108 as a closed nerve conduit 410 in FIG. 6. After the manifolds 120, 220 are inserted in the nerve damage sites 108, the closed nerve conduit 410 may be sealed by utilizing one or more stitches 415 or any other fastening device known in the art. The closed nerve conduit 410 may be composed of a bioabsorbable or a bioinert material. Materials that may be used for nerve conduits include, without limitation, polylactic acid (PLA), polyglycolic acid (PGA), polylactide-co-glycolide (PLGA), polyvinylpyrrolidone, polycaprolactone, polycarbonates, polyfumarates, caprolactones, polyamides, polysaccharides (including alginates (e.g., calcium alginate) and chitosan), hyaluronic acid, polyhydroxybutyrate, polyhydroxyvalerate, polydioxanone, polyorthoesthers, polyethylene glycols, poloxamers, polyphosphazenes, polyanhydrides, polyamino acids, polyacetals, polycyanoacrylates, polyurethanes, polyacrylates, ethylene-vinyl acetate polymers and other acyl substituted cellulose acetates and derivatives thereof, polystyrenes, polyvinyl chloride, polyvinyl fluoride, poly(vinylimidazole), chlorosulphonated polyolefins, polyethylene oxide, polyvinyl alcohol, Teflon®, and nylon. In certain aspects, biological (e.g., purified or recombinant) materials may be used to form nerve conduits including but not limited to, fibrin, fibronectin or collagen (e.g., DURAMATRIX™).

A nerve conduit 110, 410 may be an unbroken substantially tubular structure fitted across a gap between a proximal and distal nerve stump such as depicted in FIG. 6. Examples of such substantially tubular nerve conduits, also referred to as nerve guides, include without limitation NEURAGEN® and NEUROFLEX™ collagen conduits. A nerve conduit may also be formed from a wrap that is positioned around a disconnected or damaged (e.g., pinched) nerve and sealed with a closure, such as a suture. Specific examples of wrap-type nerve conduits include, without limitation, NEUROMEND™ and NEURAWRAP™ collagen conduits. In certain aspects, the nerve conduit is made of a material that encloses the damaged nerve, so as to exclude infiltration of non-nerve cells such as glia. In some embodiments, the nerve conduit material is permeable, thereby allowing fluid and protein factors to diffuse through the conduit. For example, the pores in a nerve conduit may be sufficiently small so as to exclude the entry of cells into the conduit lumen (e.g., pores having an interior diameter or average interior diameter of between about 5 µm and 50 µm, 10 µm and 30 µm or 10 µm and 20 µm). Thus, when reduced pressure is applied to the interior of the conduit fluid and proteins may be drawn to the lumen of the conduit by the pressure gradient. The skilled artisan will recognize that the dimensions of the conduit may be adjusted for any particular nerve application. Generally, the conduits comprise an internal diameter of less than about 6.0 mm, such as about 5, 4, 3, 2.5 or 2 mm.

Referring to FIG. 7, the reduced-pressure systems 100, 200, 700 may further comprise a pressure sensor 740 operably connected to the first conduit 125 to measure the reduced pressure being applied to the manifolds 120, 220. The systems 100, 200, 700 may further include a control unit 745 electrically connected to the pressure sensor 740 and the reduced pressure source 115. The pressure sensor 740 measures the reduced pressure within the nerve gap 114 and also may indicate whether the first conduit 125 is occluded with blood or other bodily fluids. The pressure sensor 740 also provides feedback to control unit 745 which regulates the reduced pressure therapy being applied by the reduced pressure source 115 through the first conduit 125 to the manifolds 120, 220. The reduced-pressure systems 100, 200, 700 may also comprise a fluid supply 750 fluidly coupled to the first conduit 125 via a second conduit 752 and operatively connected to the control unit 745. The fluid supply 750 may be used to deliver growth and/or healing agents to the nerve damage site 108 including, without limitation, an antibacterial agent, an antiviral agent, a cell-growth promotion agent, an irrigation fluid, antibodies or other chemically active agents. The systems 100, 200, 700 further comprises a first valve 754 positioned in the second conduit 752 to control the flow of fluid therethrough, and a second valve 756 positioned in the first conduit 125 between the reduced pressure source 115 and the juncture between the first conduit 125 and the second conduit 752 to control the flow of reduced pressure. The control unit 745 is operatively connected to the first and second valves 754, 756 to control the delivery of reduced pressure and/or fluid from the fluid supply 750, respectively, to the manifolds 120, 220 as required by the particular therapy being administered to the patient. The fluid supply 150 may deliver the liquids as indicated above, but may also deliver air to the manifolds 120, 220 to promote healing and facilitate drainage at the site of the nerve damage site 108.

As used herein, the term "manifold" refers to a substance or structure that is provided to assist in directing reduced pressure to, delivering fluids to, or removing fluids from a tissue site. A manifold can include a plurality of flow channels or pathways that are interconnected to improve distribution of fluids provided to and removed from the area of tissue around the manifold. Examples of manifolds may include, without limitation, devices that have structural elements arranged to form flow channels, cellular foams such as open-cell foam, porous tissue collections, and liquids, gels and foams that include or cure to include flow channels. A detailed description of manifolds and their use according to the invention is provided below.

The term "scaffold" as used herein refers to a substance or structure applied to or in a wound or defect that provides a structural matrix for the growth of cells and/or the formation of tissue. A scaffold is often a three dimensional porous structure. The scaffold can be infused with, coated with, or comprised of cells, growth factors, extracellular matrix components, nutrients, integrins, or other substances to promote cell growth. A scaffold can take on characteristics of a manifold by directing flow through the matrix. A manifold can transmit flow to the scaffold and tissue; in the context of reduced pressure treatment, the manifold can be in fluid communication with the scaffold. A detailed description of scaffolds and their use according to the invention is provided below.

As such, the invention disclosed here discloses methods and apparatuses for controlling cellular-level based patterns of fluid flow that would allow for control of patterned protein organization at a microscopic, nanoscopic, or mesoscopic scale amenable to provide a structured manifold and, optionally, a scaffold material for cellular migration, differentiation, and like behavior necessary for functional regeneration of tissues. In comparison to the passive nature of the current state of the art with regards to tissue repair and regeneration, the methods, scaffolds, manifolds, flow sources and systems disclosed herein provide an active mechanism by which to promote the endogenous deposition of proteins and organization of the provisional matrix with biochemical and physical cues to direct cellular colonization of a scaffold or tissue space. The present invention thus enhances current technology by exploiting the active force of directed fluid flow, providing a framework upon which to design manifolds and scaffolds based upon the need of the biology under the influence of fluid flow. Flow vectors and pathways are utilized to enhance protein deposition and cellular colonization. The systems provided herein are designed to promote establishment of a provisional matrix network with a seamless transition from the healthy tissue edges through a scaffold or tissue site to promote a functional tissue continuum.

Thus, the apparatuses, methods and systems disclosed herein provide a means for active guidance of tissue regeneration through an implanted scaffold or within a tissue site to promote functional recovery. This active guidance occurs through mechanisms of controlled fluid flow, which can be used to initiate or augment the early stages of the body's own natural healing process; a manifold can provide the active guidance necessary to create a controlled fluid flow. Specifically, the controlled flow vectors that the manifolds provide can be used to facilitate the directed influx of cells and proteins into a scaffold. Creation of specific flow pathways within a tissue site or scaffold can lead to patterned deposition of proteins, such as collagen and fibrin within the manifold, scaffold or tissue space. Biochemical cues from cytokines, growth factors, and cells bound within the provisional matrix can work in conjunction with the natural physical cues of the provisional matrix and extracellular matrix to guide the subsequent migration of endogenous cells during the repair stages of healing. These cues act to establish a biological continuum that emanates from the healthy tissues and passes through the scaffolding or tissue space to facilitate a continuous guidance pathway for organized tissue regeneration.

To that end, this disclosure provides unique manifolding technologies designed for specific biological needs based upon principles of fluid flow. In certain aspects, the invention concerns a new approach to wound healing, flow (or gradient) activated tissue engineering. In rudimentary form, this approach involves a source or generator of flow that forms a gradient for controlled movement of either endogenous or exogenous fluids into, out of, or through a tissue space for the organized deposition of proteins and/or spatial concentration of cytokines and growth factors, with subsequent formation of a directionally oriented provisional matrix. The tissue space being defined here includes, but is not limited to, the region surrounding a site of nerve tissue damage.

Fluid flow into, through, or out of the nerve tissue space can be refined and directed through the inclusion of additional elements to the system including manifolds and/or scaffolds. The coordinated elements of the system are designed to create flow parameters, pathways, and patterns sufficiently detailed in scale as to be able to influence and direct the controlled adsorption of proteins, the organization of matrix, and organized colonization of specific cell types. Individual elements of the system are as follows.

Source or Generator of Flow.

Flow is induced into, through, or out of the nerve tissue space by methods or apparatuses that introduce changes in mechanical, chemical, and/or electrical potentials. These generators of flow provide either a gradient or a change in potential from the site or reservoir of endogenous or exogenous fluids to the placement position of the flow generator or its extension element (i.e., manifold or scaffold). In one embodiment, the source of flow comprises a source of reduced pressure. Systems and apparatuses according to the invention may also comprise valves or arrays of valves that control the application and amount of negative pressure applied to the manifold. In certain aspects, nerve conduits and/or manifolds described herein comprise a pressure sensor. Thus, in some embodiments, the amount of negative pressure applied by a source is regulated based on the amount of negative pressure that is sensed in the manifold or nerve conduit or at the site of tissue damage.

Manifold.

The flow generators are the driving force for stimulating the flow of fluids. Manifolds are apparatuses for refining the pattern of flow between the source or generator of flow and the tissue space. The macroscale level of flow is refined by specialized manifolds utilized for directed localization to a single point or to a plurality of selectively positioned points for creating initiation sites for microscale flow pathways within the manifold/scaffold and, ultimately, the tissue space. The manifold may also serve as a conduit for the removal of fluids from and as an apparatus for the delivery of exogenous fluids to the tissue space.

A manifold generally refers to a physical substance or structure that serves to assist in applying and translating a mechanical, chemical, electrical or similar alterations into changes in the flow of a fluid, herein defined as the movement of liquids, gases, and other deformable substances such as proteins, cells, and other like moieties. As such; this physical device includes a single point or plurality of points for the egress or evacuation of pressure, fluids, and like substances capable of translating the movement of fluids in a scaffold, as defined above. This can include, but is not limited to, the introduction of exogenous factors such as cells and/or therapeutic moieties into the scaffold through the lumen or plurality of lumens present in the manifold. In addition, as used herein, a manifold includes a single point or plurality of points for the ingress or introduction of fluid from the scaffold back toward the point source of flow.

Flow distributed by the manifold can direct the movement of endogenous proteins, growth factors, cytokines, and cells from their resident locations within the host to the tissue space or scaffold in an organized manner. The establishment of flow along these pathways leads to the deposition of proteins and provisional matrix that creates an interfacial endogenous network connecting the host to the scaffold. Extensions of this matrix can be established within the scaffold through selective positioning of the manifold flow initiation sites with flow promoting scaffolding designs. The organized protein deposition and provisional matrix provide a biochemical and physical framework that stimulates the attachment and migration of cells along directed pathways throughout the scaffold and the tissue space. The resulting endogenous network of proteins, growth factors, and cells provides a foundation upon which subsequent phases of the body's own tissue repair and regeneration mechanisms can build.

When in place, the manifold works in conjunction with a flow generating source and a scaffold, if present. Flow generating sources include, but are not limited to generators of negative pressure; generators of positive pressure; and generators of osmotic flow. The flow gradient established in the manifold may be further refined through the scaffold, to deliver a flow gradient to the scaffold to optimize flow through the scaffold as needed for the particular defect. Many of the embodiments disclosed herein are manifolds capable of translating changes in pressure and the like into controlled movement of fluids, optionally through a physical scaffold, for the purposes of directed tissue regeneration. These embodiments are generally specified for a particular application in the regeneration of specific tissues, but are not limited to a particular tissue therein.

In order to realize the goal of inducing flow for the purpose of tissue regeneration, alterations in the aforementioned mechanical, chemical, or electrical impetus must be translated from the singular gradient source toward a physical substrate or scaffold to elicit cellular-level changes in protein adsorption, matrix organization, cell migration, and other tissue regeneration-related behaviors. These alterations are multivariate in nature and can include mechanical changes that elicit a physical change in pressure applied to the scaffold as applied to the site of the wound or desired site of tissue regeneration, chemical changes that elicit a gradient in protein and/or ion concentrations, which result in the creation of osmotic gradients capable of inducing flow, or electrical changes that create a gradient of current/ion exchange allowing for propagation of electrical signals from the point source. It is to be understood, however, that the applicants are not bound by any particular mechanism through which gradients and fluid flow induce advantageous results in tissue repair or growth. In order to advantageously transmit these gradients to the tissue, a physical device is needed to direct the path of flow from its source to the scaffold or tissue site and vice versa.

In some embodiments, the manifold comprises a physical structure in close apposition to or within the contents of a scaffold and serves to propagate an alteration in a physical parameter, whether it be mechanical, chemical, electrical, or something similar in nature, for the means of directing these changes from its point source to the scaffolding material. The placement of this manifold with respect to its location with regard to that of the scaffold may be of crucial importance for facilitating controlled and directed regeneration of specific tissue types. For example, in peripheral nerve where regeneration primarily occurs in a unidirectional manner from the proximal to distal nerve stumps, it may be important to place the manifold along the length of a nerve conduit more toward it distal end to help direct regeneration toward that end. However, it may also be important to not place the manifold at the most distal aspect of the scaffold/conduit as soluble factors derived from the distal stump have been shown to be important for directing nerve regeneration toward its source.

Manifolds may be composed of a bioabsorbable or bioinert material. Examples include non-bioabsorbable materials such as medical grade silicone polymers, metals, polyvinylchloride (PVC), and polyurethane. Bioabsorbable polymers such as collagen, polylactic acid (PLA), polyglycolic acid (PGA), polylactide-co-glycolide (PLGA), a polysaccharide, a hydroxyapatite, or a polyethylene glycol, or combinations thereof, can also be used. Some manifolds are also a mix of non-bioresorbable and bioresorbable materials. In general material used for a scaffold may also be used to compose a manifold and such materials are further detailed below. In certain aspects, manifold materials are structured to include a high void fraction for improved bioabsorption properties.

Support.

Manifold support structures, such as a manifold chamber and/or flange may be composed of any acceptable biocompatible material. A support structure will typically be impermeable and surround the manifold so as to maintain manifold pressure.

A portion of the support, such as a flange, couples the manifold and the nerve conduit. In certain aspects, a flange is attached to the exterior surface of a nerve conduit with an adhesive such as a fibrin glue, cyanoacrylate, or other biologically derived adhesive. A support may also be connected to a nerve conduit via reversible mechanisms other than an adhesive, such as chemical, thermal, osmotic, mechanical (snap or other interference fit, threaded, etc), magnetic, and electrostatic mechanisms. The manifold may be used to deliver agents that reverse the action of the binding mechanism in order to detach the support from the nerve conduit (e.g., upon completion of therapy). For example, electrostatic binding may be released through introduction of salt solutions or biocompatible solvents may be used to release adhesives.

Scaffold.

Biologic and synthetic scaffolds are used in the field of tissue engineering to support protein adhesion and cellular ingrowth for tissue repair and regeneration. The current state of the art in scaffold technology relies upon the inherent characteristics of the surrounding tissue space for the adsorption of proteins and migration of cells. A scaffold for use according to the invention is coupled to a manifold, provides physical guidance to direct the pathway of fluid flow in the tissue site, creating avenues for the movement and migration of adhesive proteins and cells, respectively, which are integral to the establishment of a provisional matrix in predetermined patterns of organization within the tissue space. The methods and apparatuses described for fluid flow-induced and gradient-induced generation of tissues have direct implications into the design of the scaffolds. Within this context, scaffolds serve to refine the pathways of fluid flow within the tissue space to cellular level patterns from the fluid source to the point(s) of flow initiation within the manifold. A scaffold may embody characteristics of a manifold or be combined in conjunction with a manifold for refinement of the flow pathways within the tissue site. In certain aspects, a scaffold is a reticulated structure comprising high void fraction for improved bioabsorption properties.

Scaffolds may also comprise retention structures as described herein such as funnel guides and fiber guides. For example, funnel guides may be used to direct the diffusion and/or migration of cells or growth factors at a site of nerve damage. In some cases, multiple funnel guides such as 2, 3, 4, 5, 6, 7, 8 or more funnel guides are comprised in a scaffold. A funnel guide may be composed of a hydrophobic material and may be bioabsorbable so as to degrade as nerve tissue grows into the site of the nerve damage. Funnel guides may also be hydrophilic to assist in the directed movement of slow moving fluids e.g., by wicking. Funnel guides may also have bioabsorption properties that differ from the narrow to the wide end of the funnel guide. For instance, the narrow end of the funnel guide may be absorbed at a faster rate so that the aperture of the narrow end becomes wider as tissue regrowth occurs. Likewise, in aspects where multiple funnel guides are comprised in a scaffold, funnel guides closer to the proximal end of the nerve damage site may be composed of a material that is absorbed at a faster rate so that funnel structures closer to the proximal end of a nerve damage site are absorbed more rapidly.

Fiber guides in scaffolds may also be composed of bioabsorbable material such that the guides are absorbed as tissue growth or regrowth occurs. As detailed above, fiber guides may comprise protrusions (e.g., barbs) or hook structures and may be essentially linear or form a spiral as they extend through the scaffold at the nerve damage site. In certain aspects, the fiber guides and associated structures (e.g., fiber protrusions and hooks) direct cell growth or migration at the site of nerve damage. In some embodiments, the fiber structures comprise bioactive molecules as part of their structure. For example, fiber structures may comprise growth factors that enhance cell growth along the length of the fibers or binding moieties (such as antibodies) that bind cells or growth factors to the fibers to enhance the growth or regrowth of nerve tissue.

Nonlimiting examples of suitable scaffold, funnel and fiber materials include extracellular matrix proteins such as fibrin, collagen or fibronectin, and synthetic or naturally occurring polymers, including bioabsorbable or non-bioabsorbable polymers, such as polylactic acid (PLA), polyglycolic acid (PGA), polylactide-co-glycolide (PLGA), polyvinylpyrrolidone, polycaprolactone, polycarbonates, polyfumarates, caprolactones, polyamides, polysaccharides (including alginates (e.g., calcium alginate) and chitosan), hyaluronic acid, polyhydroxybutyrate, polyhydroxyvalerate, polydioxanone, polyethylene glycols, poloxamers, polyphosphazenes, polyanhydrides, polyamino acids, polyortho esters, polyacetals, polycyanoacrylates, polyurethanes, polyacrylates, ethylenevinyl acetate polymers and other acyl substituted cellulose acetates and derivatives thereof, polystyrenes, polyvinyl chloride, polyvinyl fluoride, poly(vinylimidazole), chlorosulphonated polyolefins, polyethylene oxide, polyvinyl alcohol, Teflon®, and nylon. The scaffold can also comprise ceramics such as hydroxyapatite, corallin apatite, calcium phosphate, calcium sulfate, calcium carbonate or other carbonates, bioglass, allografts, autografts, xenografts, decellularized tissues, or composites of any of the above. In particular embodiments, the scaffold comprises collagen, polylactic acid (PLA), polyglycolic acid (PGA), polylactide-co-glycolide (PLGA), a polyurethane, a polysaccharide, an hydroxyapatite, or a polytherylene glycol. Additionally, the scaffold can comprise combinations of any two, three or more materials, either in separate areas of the scaffold, or combined noncovalently, or covalently (e.g., copolymers such as a polyethylene oxide-polypropylene glycol block copolymers, or terpolymers), or combinations thereof. Suitable matrix materials are discussed in, for example, Ma and Elisseeff, 2005, and Saltzman, 2004.

Bioactive Agents

In certain aspects, the apparatuses and methods according to the invention concern bioactive agents. Bioactive agents may, in some cases, be incorporated directly onto a manifold or scaffold material (i.e., to generate a bioactive manifold and/or scaffold). For example, agents that facilitate tissue growth such as collagen or fibrin may be directly incorporated onto or into a manifold or scaffold material. Likewise, in applications where aberrant immune response need be avoided (e.g., tissue grafts) immune regulator agents such as rapamycin may be incorporated into manifold or scaffold structures.

In further aspects soluble bioactive agents may be introduced at a site of tissue damage by virtue of flow through the tissue site. For example, a manifold may be in fluid communication with a fluid source and a bioactive agent may be introduced into the fluid source and thereby into the manifold and damaged nerve tissue.

Nonlimiting examples of useful bioactive growth factors for various applications are growth hormone (GH), a bone morphogenetic protein (BMP), transforming growth factor-α(TGF-α), a TGF-β, a fibroblast growth factor (FGF), granulocyte-colony stimulating factor (G-CSF), granulocyte/macrophage-colony stimulating factor (GM-CSF), epidermal growth factor (EGF), platelet derived growth factor (PDGF), insulin-like growth factor (IGF), vascular endothelial growth factor (VEGF), hepatocyte growth factor/scatter factor (HGF/SF), an interleukin, tumor necrosis factor-α(TNF-α) or nerve growth factor (NGF).

Nerve Tissue Repair and Engineering.

The apparatuses and systems disclosed herein can be used for nerve tissue repair and engineering in various contexts including the following.

Repair and Regeneration of Lost Tissue.

A generator of flow may be combined with manifolds and/or scaffolds to direct the regeneration of lost tissue at a site of injury or compromised function. Tissues lost from traumatic injury, surgery, burns, or other causes (e.g., infection or autoimmune disease) can be led to regenerate using the methods, scaffolds, manifolds, flow sources and systems of the invention. Functional nerve tissue is directed to regenerate.

Retard the Progression of a Tissue Disease State.

A generator of flow may be combined with manifolds and/or scaffolds to retard disease progression of an affected nerve tissue such as occurs, e.g., in autoimmune disease.

Maintenance of Tissue Viability.

A generator of flow may be combined with manifolds and/or scaffolds to maintain the viability of explanted tissues either for in vitro study, ex vivo scaffold or implant preparation, or in vivo transplant. A generator of flow combined with a manifold may be used to provide fluid flow to the tissue and to control waste removal from the tissue.

Expansion of Tissue.

A generator of flow may be combined with manifolds and/or scaffolds to promote the expansion of existing tissues. The methods, scaffolds, manifolds, flow sources and systems of the invention can be used to direct the growth of tissues where additional tissue quantity is needed or desired Acceleration of Tissue Formation.

A generator of flow may be combined with manifolds and/or scaffolds to accelerate the rate of tissue formation within a natural healing response. The methods, scaffolds, manifolds, flow sources and systems of the invention may be used to accelerate tissue growth by augmenting formation of provisional matrices, facilitating its stable positioning, and aiding in recruitment of cells to the tissue space.

Stimulating Differentiation of Stem Cells Along Specific Pathways.

A generator of flow may be combined with manifolds and/or scaffolds to stimulate differentiation of stem cells or other pluripotent cells into specific lineages. Application of flow using the methods, scaffolds, manifolds, flow sources and systems of the invention may be used to direct pluripotent cells into specific cell lineages needed to foster growth in the tissue space.

Introducing Proteins, Matrix, Cells, or Pharmaceuticals into the In Vivo Environment.

A generator of flow may be combined with manifolds and/or scaffolds to introduce exogenous growth factors, proteins, cells, or pharmaceutical agents into the tissue space to augment tissue repair, regeneration, and/or maintenance.

Creating Matrices In Vitro for Implantation In Vivo.

A generator of flow may be combined with manifolds and/or scaffolds to facilitate formation of matrices in vitro that may subsequently be used for in vivo transplantation.

Promoting Integration of Transplanted Tissue.

A generator of flow may be combined with manifolds and/or scaffolds to promote integration of transplanted tissue into the host environment. This can be applied to autograft, allograft, or xenograft transplants.

Directing Extracellular Matrix (ECM) Deposition and Orientation In Vitro.

A flow generator may be combined with manifolds and/or scaffolds to guide the directed deposition and orientation of ECM expressed by cells and tissues. The directed orientation of ECM has an impact in organizing and directing the attachment and colonization of subsequent cell layers and tissues.

REFERENCES

U.S. Pat. No. 4,787,906
U.S. Pat. No. 6,103,255
U.S. Pat. No. 6,135,116
U.S. Pat. No. 6,365,146
U.S. Pat. No. 6,695,823
U.S. Pat. No. 6,696,575
U.S. Pat. No. 6,767,334
U.S. Pat. No. 6,814,079
U.S. Pat. No. 6,856,821
U.S. Pat. No. 6,936,037
U.S. Pat. No. 6,951,553
U.S. Pat. No. 6,994,702
U.S. Pat. No. 7,004,915
U.S. Pat. No. 7,070,584
U.S. Pat. No. 7,077,832
U.S. Pat. No. 7,108,683
U.S. Pat. No. 7,160,553
U.S. Pat. No. 7,186,244
U.S. Pat. No. 7,214,202
U.S. Pat. No. 7,279,612
U.S. Pat. No. 7,316,672
U.S. Pat. No. 7,346,945
U.S. Pat. No. 7,351,250
U.S. Pat. No. 7,384,786
U.S. Patent Publn. 2003/0225347
U.S. Patent Publn. 2005/0260189
U.S. Patent Publn. 2007/0123895
U.S. Patent Publn. 2008/0033324
U.S. Patent Publn. 2008/0208358
U.S. Provisional Patent Appln. 61/142,053
U.S. Provisional Patent Appln. 61/142,065
Anderson et al., *Tissue Eng.*, 13:2525-38, 2007.
Brody et al., *J. Biomed. Mater. Res. B: Appl. Biomater.*, 83:16-43, 2007.
Gemmiti et al., *Tissue Eng.*, 12:469-79, 2006.
Lago et al., *IEEE Trans. Biomed. Eng.*, 54:1129-37, 2007.
Ma et al., *Scaffolding in Tissue Engineering*, 2005.
Manwaring et al., *Biomaterials*, 22:3155-3168, 2001.
Manwaring et al., *Biomaterials*, 25:3631-3638, 2004.
Mercier et al., *Biomaterials*, 26:1945-1952, 2005.
Mikos et al., *J. Biomed. Mater. Ref*, 27:183-189, 2004.
Norman et al., *Ann Biomed Eng.*, 34:89-101, 2006.
PCT Appln. WO 00/38755A2
PCT Appln. WO 00/61206A1
PCT Appln. WO 03/018098A2
PCT Appln. WO 03/092620A2
PCT Appln. WO 04/060148A2
PCT Appln. WO 04/105576A2
PCT Appln. WO 05/009488A2
PCT Appln. WO 05/033273A2
PCT Appln. WO 06/004951
PCT Appln. WO 06/127853
PCT Appln. WO 07/067,685A2
PCT Appln. WO 07/092,397A2
PCT Appln. WO 07/106,589A2
PCT Appln. WO 07/106,590A2
PCT Appln. WO 07/106,591A2
PCT Appln. WO 07/106,592A2
PCT Appln. WO 07/106,594A2
PCT Appln. WO 07/133,555A2
PCT Appln. WO 07/133,556A2
PCT Appln. WO 07/143,060A2
PCT Appln. WO 07/196,590
PCT Appln. WO 08/013,896A2
PCT Appln. WO 08/036,162A2
PCT Appln. WO 08/036359A2
PCT Appln. WO 08/036,361A2
PCT Appln. WO 08/042,481A2
PCT Appln. WO 08/091,521A2
Pfister et al., *Neurosurgery*, 60:137-41, 2007.
Saltzman, *Tissue Engineering: Engineering Principles for the Design of Replacement Organs and Tissues*, 2004.
Sachlos et al., *Cells and Mat.*, 5:29-40, 2003.
Segvich et al., *J. Biomed. Mater. Res. B: Appl. Biomater.*, 848:340-349, 2008.
Shimko et al., *J Biomed Mater. Res. B: Appl. Biomater.*, 73:315-24, 2005.
Takahashi et al., *Cell*, 126:663-76, 2006.
Tan et al., *Bone*, 41:745-751, 2007.
Tan et al., *Biochem. Biophys. Res. Comm.*, 369:1150-1154, 2008.
Walsh et al., *Tissue Eng.*, 11:1085=1094, 2005.
Wen et al., *Handbook of Nanostructured Biomaterials and Their Applications in Nanobiotechnology*, 1-23, 2005.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

In view of the above, it will be seen that the advantages of the invention are achieved and other advantages attained. As various changes could be made in the above methods and compositions without departing from the scope of the invention, it is intended that all matter contained in the above description and shown in the accompanying drawings shall be interpreted as illustrative and not in a limiting sense.

We claim:

1. A system for providing reduced pressure to a defect at a tissue site of a nerve, the system comprising:
a pressure source for supplying the reduced pressure;
a nerve conduit having a generally tubular shape and having a luminal wall for surrounding the tissue site to contain fluids within a luminal space between the tissue site and the luminal wall;
a manifold fluidly coupled to the pressure source to distribute the reduced pressure to the defect; and
a scaffold comprising at least one scaffold guide having a frustum-shaped conical tubular member with a base opening at one end and a vertex opening at the other end wherein the at least one scaffold guide is positioned within the luminal space in fluid communication with the manifold and oriented therein with the vertex opening positioned closer to the manifold than the base opening, and at least one fiber guide extending longitudinally through the luminal space and the vertex opening of the at least one scaffold guide;

whereby the at least one scaffold guide facilitates tissue growth at the tissue site by organizing matrix deposition, promoting cell binding, or guiding the migration of cells through the luminal space.

2. The system of claim 1, wherein the defect is a severed nerve.

3. The system of claim 1, wherein the defect is a pinched, partially severed, or degenerative nerve and the at least one scaffold guide is adapted to receive the nerve through the vertex opening of the at least one scaffold guide.

4. The system of claim 1, wherein the at least one scaffold guide is substantially non-porous.

5. The system of claim 1, wherein the at least one scaffold guide comprises pores that are sufficiently small to collect cells.

6. The system of claim 1, wherein the at least one scaffold guide is composed of a hydrophobic material.

7. The system of claim 1, wherein the at least one fiber guide is adapted to be in fluid communication with the tissue site of the nerve.

8. The system of claim 1, wherein the at least one fiber guide is in fluid communication with the manifold and the at least one scaffold guide.

9. The system of claim 1, wherein the at least one fiber guide comprises fibrous protrusions extending into the luminal space.

10. The system of claim 1, wherein the at least one fiber guide is linear.

11. The system of claim 1, wherein the at least one fiber guide is bioabsorbable.

12. The system of claim 11, wherein the at least one fiber guide is comprised of collagen or fibrin.

13. The system of claim 1, wherein the manifold is adapted to be positioned adjacent a distal side of the nerve.

14. The system of claim 1, wherein the manifold provides reduced pressure preferentially to a distal side of the nerve.

15. The system of claim 1, wherein the manifold is composed of a bioinert or bioabsorbable material.

16. The system of claim 1, wherein the manifold is substantially tubular or cylindrical in shape and positioned within the luminal space of the nerve conduit.

17. The system of claim 1, wherein the manifold extends through the wall of the nerve conduit in fluid communication with the luminal space.

18. The system of claim 1, wherein the scaffold is formed from a foam or gel material.

19. The system of claim 1, wherein the scaffold comprises a bioactive agent.

20. The system of claim 19, wherein the bioactive agent is at least one of an antibiotic, an antibody and a growth factor.

21. The system of claim 19, wherein the bioactive agent is a growth hormone (GH), a bone morphogenetic protein (BMP), transforming growth factor-α (TGF-α), a TGF-β, a fibroblast growth factor (FGF), granulocyte-colony stimulating factor (G-CSF), granulocyte/macrophage-colony stimulating factor (GM-CSF), epidermal growth factor (EGF), platelet derived growth factor (PDGF), insulin-like growth factor (IGF), vascular endothelial growth factor (VEGF), hepatocyte growth factor/scatter factor (HGF/SF), an interleukin, tumor necrosis factor-α (TNF-α) or nerve growth factor (NGF).

22. The system of claim 1, wherein the nerve conduit comprises a slice along its length that forms an opening whereby the nerve conduit is implantable around the tissue site and sealable with one or more closure elements.

23. The system of claim 1, wherein the nerve conduit is composed of a bioinert material.

24. The system of claim 1, wherein the nerve conduit is composed of a bioabsorbable material.

25. The system of claim 24, wherein the nerve conduit is composed of collagen.

26. The system of claim 1, wherein the nerve conduit comprises pores.

27. The system of claim 26, wherein the pores are sufficiently small to exclude the entry of cells from tissue surrounding the nerve conduit into the luminal space.

28. The system of claim 27, wherein the pores have a diameter of between about 5 μm and about 50 μM.

* * * * *